(12) United States Patent
Linder et al.

(10) Patent No.: US 8,535,344 B2
(45) Date of Patent: *Sep. 17, 2013

(54) METHODS, SYSTEMS, AND DEVICES FOR PROVIDING EMBOLIC PROTECTION AND REMOVING EMBOLIC MATERIAL

(75) Inventors: Richard J. Linder, Sandy, UT (US); Daryl R. Edmiston, Sandy, UT (US); Steven W. Johnson, West Jordan, UT (US)

(73) Assignee: Rubicon Medical, Inc., Salt Lake City, UT (US)

( * ) Notice: Subject to any disclaimer, the term of this patent is extended or adjusted under 35 U.S.C. 154(b) by 1803 days.

This patent is subject to a terminal disclaimer.

(21) Appl. No.: 10/936,857

(22) Filed: Sep. 9, 2004

(65) Prior Publication Data
US 2005/0096692 A1 May 5, 2005

Related U.S. Application Data

(60) Provisional application No. 60/502,435, filed on Sep. 12, 2003, provisional application No. 60/503,154, filed on Sep. 15, 2003.

(51) Int. Cl.
*A61M 29/00* (2006.01)
(52) U.S. Cl.
USPC .......................................... 606/200; 623/1.11
(58) Field of Classification Search
USPC ................ 606/200, 108, 194, 198; 623/1.12, 623/1.11, 1.23
See application file for complete search history.

(56) References Cited

U.S. PATENT DOCUMENTS 3,472,230 A 10/1969 Fogarty
3,592,186 A 7/1971 Oster
3,683,904 A 8/1972 Forster (Continued)

FOREIGN PATENT DOCUMENTS

DE 28 21 048 7/1980
DE 34 17 738 11/1985

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).
"Endovascular Grafts, Stents Drive Interventional Radiology Growth," *Cardiovascular Device Update*, 2(3):1-12 (Mar. 1996).
"Protruding Atheromas in the Thoracic Aortic and Systemic Embolization," pp. 423-427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger," *AJR*, 141:601-604 (Sep. 1983).

(Continued)

*Primary Examiner* — Victor Nguyen
(74) *Attorney, Agent, or Firm* — Seager, Tufte & Wickheim LLC

(57) ABSTRACT

An embolic protection device includes a guide member having a distal end, a proximal end, and a lumen extending from the distal end to the proximal end. Additionally, the embolic protection device includes a filter assembly having a plurality of struts extending from the distal end of the guide member. The filter assembly further includes a filter media adapted to filter material from a blood stream coupled to at least two of the plurality of struts. The filter media can have an open proximal end and a closed distal end. The device can also include a sleeve at least partially surrounding the plurality of struts and the filter media for restraining the filter device in a collapsed position during an insertion procedure. The embolic protection device can also include additional loops of material surrounding the struts and a tether wire securing the sleeve and loops in the collapsed position.

30 Claims, 13 Drawing Sheets

(56) References Cited

U.S. PATENT DOCUMENTS

| | | | | |
|---|---|---|---|---|
| 3,889,657 | A | 6/1975 | Baumgarten | |
| 3,952,747 | A | 4/1976 | Kimmell, Jr. | |
| 3,996,938 | A | 12/1976 | Clark, III | |
| 4,046,150 | A | 9/1977 | Schwartz et al. | |
| 4,195,637 | A | 4/1980 | Gruntzig et al. | 128/348 |
| 4,271,839 | A | 6/1981 | Fogarty et al. | 128/344 |
| 4,307,722 | A | 12/1981 | Evans | 128/344 |
| 4,323,071 | A | 4/1982 | Simpson et al. | 128/343 |
| 4,367,747 | A | 1/1983 | Witzel | 128/344 |
| 4,413,989 | A | 11/1983 | Schjeldahl et al. | 604/96 |
| 4,425,908 | A | 1/1984 | Simon | |
| 4,447,227 | A | 5/1984 | Kotsanis | |
| 4,468,224 | A | 8/1984 | Enzmann et al. | 604/247 |
| 4,540,404 | A | 9/1985 | Wolvek | 604/96 |
| 4,552,554 | A | 11/1985 | Gould et al. | 604/51 |
| 4,580,568 | A | 4/1986 | Gianturco | |
| 4,590,938 | A | 5/1986 | Segura et al. | |
| 4,619,246 | A | 10/1986 | Molgaard-Nielsen et al. | |
| 4,631,052 | A | 12/1986 | Kensey | |
| 4,643,184 | A | 2/1987 | Mobin-Uddin | |
| 4,650,466 | A | 3/1987 | Luther | |
| 4,662,885 | A | 5/1987 | DiPisa, Jr. | |
| 4,705,517 | A | 11/1987 | DiPisa, Jr. | |
| 4,706,671 | A | 11/1987 | Weinrib | |
| 4,723,549 | A | 2/1988 | Wholey et al. | |
| 4,728,319 | A | 3/1988 | Masch | |
| 4,733,665 | A | 3/1988 | Palmaz | |
| 4,744,366 | A | 5/1988 | Jang | 128/344 |
| 4,748,982 | A | 6/1988 | Horzewski et al. | 128/344 |
| 4,762,129 | A | 8/1988 | Bonzel | 128/344 |
| 4,771,777 | A | 9/1988 | Horzewski et al. | 128/344 |
| 4,790,812 | A | 12/1988 | Hawkins, Jr. et al. | |
| 4,790,813 | A | 12/1988 | Kensey | |
| 4,793,348 | A | 12/1988 | Palmaz | 128/325 |
| 4,794,928 | A | 1/1989 | Kletschka | |
| 4,794,931 | A | 1/1989 | Yock | |
| 4,800,882 | A | 1/1989 | Gianturco | |
| 4,807,626 | A | 2/1989 | McGirr | |
| 4,842,579 | A | 6/1989 | Shiber | |
| 4,857,045 | A | 8/1989 | Rydell | |
| 4,857,046 | A | 8/1989 | Stevens et al. | |
| 4,867,157 | A | 9/1989 | McGurk-Burleson et al. | |
| 4,873,978 | A | 10/1989 | Ginsburg | |
| 4,886,061 | A | 12/1989 | Fischell et al. | |
| 4,898,575 | A | 2/1990 | Fischell et al. | |
| 4,907,336 | A | 3/1990 | Gianturco | |
| 4,921,478 | A | 5/1990 | Solano et al. | |
| 4,921,484 | A | 5/1990 | Hillstead | |
| 4,926,858 | A | 5/1990 | Gifford, III et al. | |
| 4,946,466 | A | 8/1990 | Pinchuk et al. | 606/194 |
| 4,950,277 | A | 8/1990 | Farr | |
| 4,955,895 | A | 9/1990 | Sugiyama et al. | |
| 4,957,482 | A | 9/1990 | Shiber | |
| 4,964,409 | A | 10/1990 | Tremulis | 128/657 |
| 4,969,890 | A | 11/1990 | Sugita et al. | 606/192 |
| 4,969,891 | A | 11/1990 | Gewertz | |
| 4,979,951 | A | 12/1990 | Simpson | |
| 4,983,167 | A | 1/1991 | Sahota | 606/194 |
| 4,986,807 | A | 1/1991 | Farr | |
| 4,998,539 | A | 3/1991 | Delsanti | |
| 5,002,560 | A | 3/1991 | Machold et al. | |
| RE33,569 | E | 4/1991 | Gifford, III et al. | |
| 5,007,896 | A | 4/1991 | Shiber | |
| 5,007,917 | A | 4/1991 | Evans | |
| 5,011,488 | A | 4/1991 | Ginsburg | |
| 5,019,088 | A | 5/1991 | Farr | |
| 5,026,377 | A | 6/1991 | Burton et al. | 606/108 |
| 5,040,548 | A | 8/1991 | Yock | 128/898 |
| 5,041,126 | A | 8/1991 | Gianturco | |
| 5,053,008 | A | 10/1991 | Bajaj | |
| 5,053,044 | A | 10/1991 | Mueller et al. | |
| 5,061,267 | A | 10/1991 | Zeiher | 606/40 |
| 5,071,407 | A | 12/1991 | Termin et al. | |
| 5,071,425 | A | 12/1991 | Gifford, III et al. | |
| 5,085,662 | A | 2/1992 | Willard | |
| 5,087,265 | A | 2/1992 | Summers | |
| 5,100,423 | A | 3/1992 | Fearnot | |
| 5,100,424 | A | 3/1992 | Jang et al. | |
| 5,100,425 | A | 3/1992 | Fischell et al. | |
| 5,102,390 | A | 4/1992 | Crittenden et al. | 604/96 |
| 5,102,415 | A | 4/1992 | Guenther et al. | |
| 5,104,399 | A | 4/1992 | Lazarus | |
| 5,108,419 | A | 4/1992 | Reger et al. | |
| 5,133,733 | A | 7/1992 | Rasmussen et al. | |
| 5,135,487 | A | 8/1992 | Morrill et al. | 604/96 |
| 5,135,531 | A | 8/1992 | Shiber | |
| 5,135,535 | A | 8/1992 | Kramer | 606/194 |
| 5,152,771 | A | 10/1992 | Sabbaghian et al. | |
| 5,152,777 | A | 10/1992 | Goldberg et al. | |
| 5,156,594 | A | 10/1992 | Keith | 604/96 |
| 5,160,342 | A | 11/1992 | Reger et al. | |
| 5,171,233 | A | 12/1992 | Amplatz et al. | |
| 5,180,367 | A | 1/1993 | Kontos et al. | 604/101 |
| 5,190,546 | A | 3/1993 | Jervis | |
| 5,195,955 | A | 3/1993 | Don Michael | |
| 5,209,729 | A | 5/1993 | Hofmann et al. | 604/96 |
| 5,209,730 | A | 5/1993 | Sullivan | 604/96 |
| 5,224,953 | A | 7/1993 | Morgentaler | |
| 5,226,909 | A | 7/1993 | Evans et al. | 606/159 |
| 5,232,445 | A | 8/1993 | Bonzel | 604/96 |
| 5,271,415 | A | 12/1993 | Foerster et al. | 128/772 |
| 5,275,151 | A | 1/1994 | Shocket et al. | 128/4 |
| 5,279,560 | A | 1/1994 | Morrill et al. | 604/96 |
| 5,300,025 | A | 4/1994 | Wantink | 604/96 |
| 5,306,286 | A | 4/1994 | Stack et al. | |
| 5,311,858 | A | 5/1994 | Adair | 128/4 |
| 5,314,444 | A | 5/1994 | Gianturco | |
| 5,314,472 | A | 5/1994 | Fontaine | |
| 5,315,996 | A | 5/1994 | Lundquist | 128/642 |
| 5,318,576 | A | 6/1994 | Plassche, Jr. et al. | |
| 5,320,605 | A | 6/1994 | Sahota | 604/101 |
| 5,328,472 | A | 7/1994 | Steinke et al. | 604/102 |
| 5,329,942 | A | 7/1994 | Gunther et al. | |
| 5,330,484 | A | 7/1994 | Gunther | |
| 5,330,500 | A | 7/1994 | Song | |
| 5,342,297 | A | 8/1994 | Jang | 604/53 |
| 5,350,398 | A | 9/1994 | Pavcnik et al. | |
| 5,354,310 | A | 10/1994 | Garnic et al. | |
| 5,356,423 | A | 10/1994 | Tihon et al. | |
| 5,364,357 | A | 11/1994 | Aase | 604/96 |
| 5,366,464 | A | 11/1994 | Belknap | |
| 5,366,473 | A | 11/1994 | Winston et al. | |
| 5,370,657 | A | 12/1994 | Irie | |
| 5,370,683 | A | 12/1994 | Fontaine | |
| 5,376,100 | A | 12/1994 | Lefebvre | |
| 5,380,283 | A | 1/1995 | Johnson | 604/96 |
| 5,383,887 | A | 1/1995 | Nadal | |
| 5,383,892 | A | 1/1995 | Cardon et al. | |
| 5,383,926 | A | 1/1995 | Lock et al. | |
| 5,387,226 | A | 2/1995 | Miraki | 606/194 |
| 5,387,235 | A | 2/1995 | Chuter | |
| 5,395,332 | A | 3/1995 | Ressemann et al. | 604/96 |
| 5,395,349 | A | 3/1995 | Quiachon et al. | |
| 5,397,345 | A | 3/1995 | Lazarus | |
| 5,399,165 | A | 3/1995 | Paul, Jr. | 604/95 |
| 5,405,377 | A | 4/1995 | Cragg | |
| 5,405,378 | A | 4/1995 | Strecker | 623/1 |
| 5,409,454 | A | 4/1995 | Fischell et al. | |
| 5,409,458 | A | 4/1995 | Khairkhahan et al. | 604/96 |
| 5,415,630 | A | 5/1995 | Gory et al. | |
| 5,419,774 | A | 5/1995 | Willard et al. | |
| 5,421,832 | A | 6/1995 | Lefebvre | |
| 5,423,742 | A | 6/1995 | Theron | |
| 5,423,885 | A | 6/1995 | Williams | |
| 5,425,765 | A | 6/1995 | Tiefenbrun et al. | |
| 5,437,288 | A | 8/1995 | Schwartz et al. | 128/772 |
| 5,441,483 | A | 8/1995 | Avitall | 604/95 |
| 5,443,498 | A | 8/1995 | Fontaine | |
| 5,449,372 | A | 9/1995 | Schmaltz et al. | |
| 5,456,667 | A | 10/1995 | Ham et al. | |
| 5,456,694 | A | 10/1995 | Marin et al. | 606/198 |
| 5,458,613 | A | 10/1995 | Gharibadeh et al. | |
| 5,462,529 | A | 10/1995 | Simpson et al. | |
| 5,476,104 | A | 12/1995 | Sheahon | |

| | | | |
|---|---|---|---|
| 5,484,418 A | 1/1996 | Quiachon et al. | |
| 5,490,837 A | 2/1996 | Blaeser et al. | 604/96 |
| 5,490,859 A | 2/1996 | Mische et al. | 606/159 |
| 5,497,785 A | 3/1996 | Viera | 128/772 |
| 5,507,731 A | 4/1996 | Hernandez et al. | 604/264 |
| 5,507,732 A | 4/1996 | McClure et al. | 604/264 |
| 5,507,767 A | 4/1996 | Maeda et al. | |
| 5,512,044 A | 4/1996 | Duer | |
| 5,527,354 A | 6/1996 | Fontaine et al. | |
| 5,536,242 A | 7/1996 | Willard et al. | |
| 5,540,707 A | 7/1996 | Ressemann et al. | |
| 5,549,553 A | 8/1996 | Ressemann et al. | 604/96 |
| 5,549,556 A | 8/1996 | Ndondo-Lay et al. | 604/102 |
| 5,549,626 A | 8/1996 | Miller et al. | |
| 5,562,724 A | 10/1996 | Vorwerk et al. | |
| 5,569,274 A | 10/1996 | Rapacki et al. | |
| 5,569,275 A | 10/1996 | Kotula et al. | |
| 5,578,009 A | 11/1996 | Kraus et al. | 604/96 |
| 5,599,492 A | 2/1997 | Engelson | 264/167 |
| 5,605,543 A | 2/1997 | Swanson | 604/96 |
| 5,634,897 A | 6/1997 | Dance et al. | |
| 5,634,942 A | 6/1997 | Chevillon et al. | 623/1 |
| 5,658,296 A | 8/1997 | Bates et al. | |
| 5,662,671 A | 9/1997 | Barbut et al. | |
| 5,669,932 A | 9/1997 | Fischell et al. | 606/198 |
| 5,669,933 A | 9/1997 | Simon et al. | |
| 5,695,519 A | 12/1997 | Summers et al. | |
| 5,707,359 A | 1/1998 | Bufalini | 606/200 |
| 5,709,704 A | 1/1998 | Nott et al. | |
| 5,720,764 A | 2/1998 | Naderlinger | |
| 5,728,066 A | 3/1998 | Daneshvar | |
| 5,746,758 A | 5/1998 | Nordgren et al. | |
| 5,749,848 A | 5/1998 | Jang et al. | |
| 5,769,816 A | 6/1998 | Barbut et al. | |
| 5,769,858 A | 6/1998 | Pearson et al. | 606/108 |
| 5,779,716 A | 7/1998 | Cano et al. | |
| 5,782,809 A | 7/1998 | Umeno et al. | 604/280 |
| 5,792,157 A | 8/1998 | Mische et al. | |
| 5,792,300 A | 8/1998 | Inderbitzen et al. | |
| 5,795,322 A | 8/1998 | Boudewijn | |
| 5,797,952 A | 8/1998 | Klein | |
| 5,800,457 A | 9/1998 | Gelbfish | |
| 5,800,525 A | 9/1998 | Bachinski et al. | |
| 5,807,330 A | 9/1998 | Teitelbaum | 604/96 |
| 5,807,398 A | 9/1998 | Shaknovich | |
| 5,810,874 A | 9/1998 | Lefebvre | |
| 5,814,064 A | 9/1998 | Daniel et al. | |
| 5,817,102 A | 10/1998 | Johnson et al. | |
| 5,817,104 A | 10/1998 | Bilitz et al. | 606/127 |
| 5,824,050 A * | 10/1998 | Karwoski et al. | 623/1.4 |
| 5,827,324 A | 10/1998 | Cassell et al. | |
| 5,833,632 A | 11/1998 | Jacobsen et al. | 600/585 |
| 5,833,644 A | 11/1998 | Zadno-Azizi et al. | |
| 5,833,650 A | 11/1998 | Imran | |
| 5,836,969 A | 11/1998 | Kim et al. | 606/200 |
| 5,843,050 A | 12/1998 | Jones et al. | 604/280 |
| 5,846,260 A | 12/1998 | Maahs | |
| 5,848,964 A | 12/1998 | Samuels | |
| 5,873,906 A | 2/1999 | Lau et al. | 623/1 |
| 5,876,367 A | 3/1999 | Kaganov et al. | |
| 5,893,867 A | 4/1999 | Bagaoisan et al. | |
| 5,895,399 A | 4/1999 | Barbut et al. | |
| 5,902,263 A | 5/1999 | Patterson et al. | |
| 5,906,618 A | 5/1999 | Larson, III | |
| 5,908,435 A | 6/1999 | Samuels | |
| 5,910,154 A | 6/1999 | Tsugita et al. | |
| 5,911,734 A | 6/1999 | Tsugita et al. | |
| 5,916,193 A | 6/1999 | Stevens et al. | |
| 5,919,225 A | 7/1999 | Lau et al. | 606/198 |
| 5,921,924 A | 7/1999 | Avitall | 600/374 |
| 5,925,016 A | 7/1999 | Chornenky et al. | |
| 5,925,060 A | 7/1999 | Forber | |
| 5,925,062 A | 7/1999 | Purdy | |
| 5,925,063 A | 7/1999 | Khosravi | |
| 5,928,203 A | 7/1999 | Davey et al. | |
| 5,928,218 A | 7/1999 | Gelbfish | |
| 5,934,284 A | 8/1999 | Plaia et al. | |
| 5,935,139 A | 8/1999 | Bates | |
| 5,938,645 A | 8/1999 | Gordon | |
| 5,941,869 A | 8/1999 | Patterson et al. | |
| 5,941,896 A | 8/1999 | Kerr | |
| 5,947,995 A | 9/1999 | Samuels | |
| 5,951,585 A | 9/1999 | Cathcart et al. | |
| 5,954,745 A | 9/1999 | Gertler et al. | |
| 5,976,172 A | 11/1999 | Homsma et al. | |
| 5,980,555 A | 11/1999 | Barbut et al. | |
| 5,989,210 A | 11/1999 | Morris et al. | |
| 5,989,271 A | 11/1999 | Bonnette et al. | |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,004,279 A | 12/1999 | Crowley et al. | 600/585 |
| 6,007,557 A | 12/1999 | Ambrisco et al. | |
| 6,007,558 A | 12/1999 | Ravenscroft et al. | 606/200 |
| 6,010,522 A | 1/2000 | Barbut et al. | |
| 6,013,085 A | 1/2000 | Howard | |
| 6,022,336 A | 2/2000 | Zadno-Azizi et al. | 604/96 |
| 6,027,520 A | 2/2000 | Tsugita et al. | |
| 6,036,717 A | 3/2000 | Mers Kelly et al. | 606/200 |
| 6,042,598 A | 3/2000 | Tsugita et al. | |
| 6,048,338 A | 4/2000 | Larson et al. | 604/523 |
| 6,051,014 A | 4/2000 | Jang | |
| 6,051,015 A | 4/2000 | Maahs | |
| 6,053,932 A | 4/2000 | Daniel et al. | |
| 6,059,814 A | 5/2000 | Ladd | |
| 6,066,149 A | 5/2000 | Samson et al. | |
| 6,066,158 A | 5/2000 | Engelson et al. | |
| 6,068,645 A | 5/2000 | Tu | |
| 6,086,605 A | 7/2000 | Barbut et al. | |
| 6,099,549 A | 8/2000 | Bosma et al. | 606/200 |
| 6,110,170 A | 8/2000 | Taylor et al. | 606/49 |
| 6,117,154 A | 9/2000 | Barbut et al. | |
| 6,126,685 A | 10/2000 | Lenker et al. | 606/194 |
| 6,129,739 A | 10/2000 | Khosravi | |
| 6,136,016 A | 10/2000 | Barbut et al. | |
| 6,142,987 A | 11/2000 | Tsugita | |
| 6,146,396 A | 11/2000 | Kónya et al. | 606/159 |
| 6,152,946 A | 11/2000 | Broome et al. | |
| 6,165,200 A | 12/2000 | Tsugita et al. | |
| 6,168,579 B1 | 1/2001 | Tsugita | |
| 6,168,603 B1 | 1/2001 | Leslie et al. | 606/200 |
| 6,168,604 B1 | 1/2001 | Cano | 606/114 |
| 6,171,327 B1 | 1/2001 | Daniel et al. | |
| 6,171,328 B1 | 1/2001 | Addis | |
| 6,174,318 B1 | 1/2001 | Bates et al. | 606/200 |
| 6,178,968 B1 | 1/2001 | Louw et al. | 128/898 |
| 6,179,851 B1 | 1/2001 | Barbut et al. | |
| 6,179,859 B1 | 1/2001 | Bates et al. | |
| 6,179,860 B1 | 1/2001 | Fulton, III et al. | 606/200 |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,217,567 B1 | 4/2001 | Zadno-Azizi et al. | 604/530 |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,254,628 B1 | 7/2001 | Wallace et al. | 623/1.12 |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,344,049 B1 | 2/2002 | Levinson et al. | |
| 6,352,561 B1 | 3/2002 | Leopold et al. | 623/1.11 |

| | | | |
|---|---|---|---|
| 6,355,051 B1 | 3/2002 | Sisskind et al. | 606/200 |
| 6,361,545 B1 | 3/2002 | Macoviak et al. | 606/200 |
| 6,383,206 B1 | 5/2002 | Gillick et al. | 606/200 |
| 6,423,086 B1 | 7/2002 | Barbut et al. | 606/200 |
| 6,447,540 B1 | 9/2002 | Fontaine et al. | 623/1.12 |
| 6,468,298 B1 | 10/2002 | Pelton | 623/1.11 |
| 6,485,501 B1 | 11/2002 | Green | 606/200 |
| 6,537,295 B2 | 3/2003 | Petersen | 606/200 |
| 6,558,396 B1 | 5/2003 | Inoue | 606/108 |
| 6,562,058 B2 | 5/2003 | Seguin et al. | 606/200 |
| 6,656,213 B2 | 12/2003 | Solem | 623/1.11 |
| 6,743,219 B1 | 6/2004 | Dwyer et al. | 604/525 |
| 6,878,153 B2* | 4/2005 | Linder et al. | 606/200 |
| 7,022,132 B2* | 4/2006 | Kocur | 623/1.11 |
| 2001/0031981 A1 | 10/2001 | Evans et al. | 606/200 |
| 2002/0016564 A1 | 2/2002 | Courtney et al. | 604/96.01 |
| 2002/0029077 A1* | 3/2002 | Leopold et al. | 623/1.11 |
| 2002/0055767 A1 | 5/2002 | Forde et al. | 623/1.11 |
| 2003/0045923 A1* | 3/2003 | Bashiri | 623/1.12 |
| 2003/0212410 A1 | 11/2003 | Stenzel et al. | 606/108 |
| 2004/0087965 A1 | 5/2004 | Levine et al. | 606/108 |
| 2004/0122464 A1* | 6/2004 | Wang et al. | 606/194 |
| 2006/0116750 A1* | 6/2006 | Hebert et al. | 623/1.11 |
| 2006/0129180 A1* | 6/2006 | Tsugita et al. | 606/200 |

FOREIGN PATENT DOCUMENTS

| | | |
|---|---|---|
| DE | 40 30 998 A1 | 10/1990 |
| DE | 4030998 C2 | 4/1991 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0564894 B1 | 10/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0737450 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 0737450 B1 | 11/2003 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 A | 5/1979 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/04875 A1 | 2/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/20064 | 4/2000 |
| WO | WO 00/49970 | 8/2000 |
| WO | WO 01/91844 | 12/2001 |

OTHER PUBLICATIONS

Cragg, Andrew et al., "Nonsurgical Placement of Arterial Endoprothesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic arch of patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

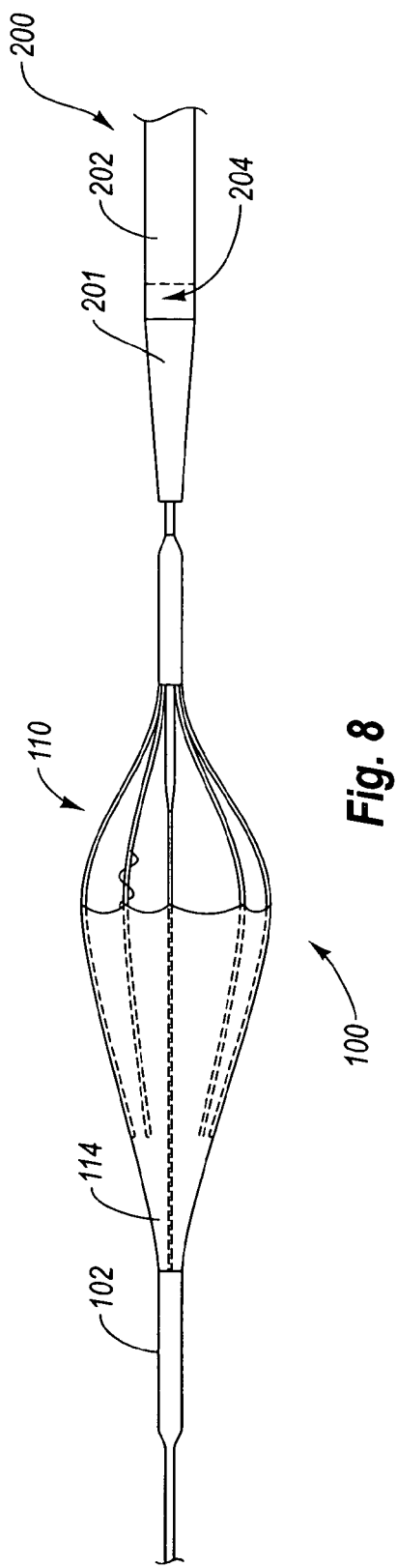
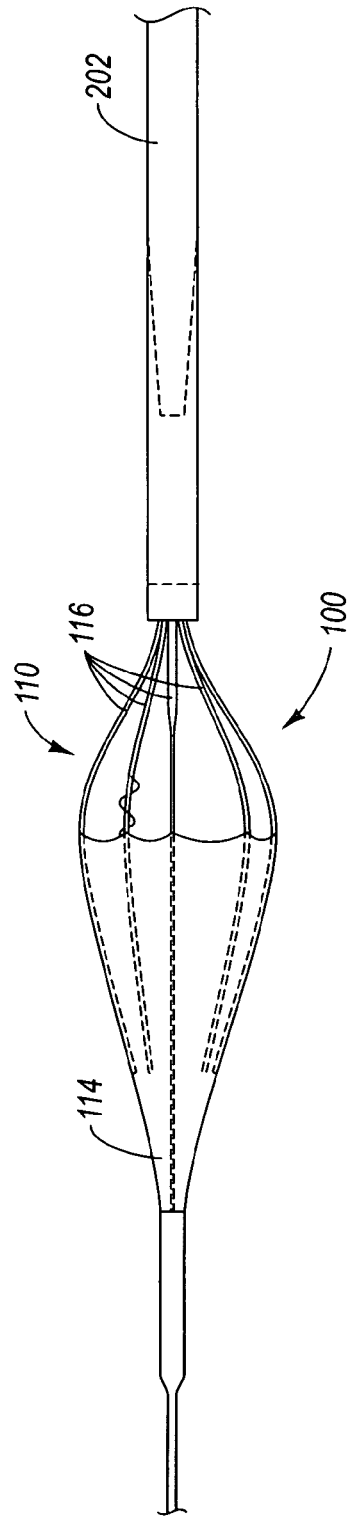

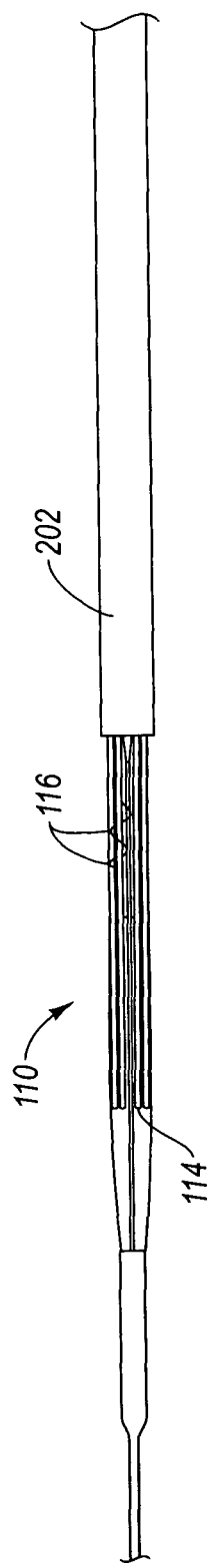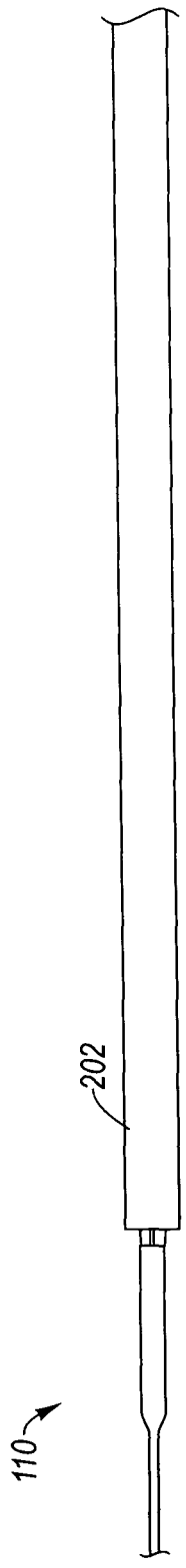
Fig. 10
Fig. 11

METHODS, SYSTEMS, AND DEVICES FOR PROVIDING EMBOLIC PROTECTION AND REMOVING EMBOLIC MATERIAL

CROSS REFERENCE TO RELATED APPLICATIONS

This application claims priority to and the benefit of U.S. Provisional Patent Application Ser. No. 60/502,435, filed on Sep. 12, 2003 and entitled "Methods, Systems and Devices for Providing Embolic Protection and Removing Embolic Material" and U.S. Provisional Patent Application Ser. No. 60/503,154, filed on Sep. 15, 2003 and entitled "Methods, Systems and Devices for Providing Embolic Protection and Removing Embolic Material", both of which are hereby incorporated by reference in their entireties. This application also relates to U.S. patent application Ser. No. 10/936,886 is now U.S. Pat. No. 7,699,865 in front of the phrase, filed Sep. 9, 2004, and entitled "Actuating Constraining Mechanism", which is incorporated herein by reference in its entirety.

BACKGROUND OF THE INVENTION

1. The Field of the Invention

The present invention relates generally to the field of percutaneous medical filters, and more specifically, to vascular embolic protection devices that are configured for percutaneous insertion into a body lumen of a patient.

2. The Relevant Technology

Human body lumens often become occluded or blocked by plaque, thrombi, other deposits, or material that reduce the blood carrying capacity of the vessel. Should the blockage occur at a critical place in the circulatory system, serious and permanent injury, and even death, can occur. To prevent this, some form of medical intervention is usually performed when significant occlusion is detected.

Several procedures are now used to open these stenosed or occluded body lumens in a patient caused by the deposit of plaque or other material on the walls of the body lumens. Angioplasty, for example, is a widely known procedure wherein an inflatable balloon is introduced into the occluded region. The balloon is inflated, dilating the occlusion, and thereby increasing the intraluminal diameter.

Another procedure is atherectomy. During atherectomy, a catheter is inserted into a narrowed artery to remove the matter occluding or narrowing the artery, i.e., fatty material. The catheter includes a rotating blade or cutter disposed in the tip thereof. Also located at the tip are an aperture and a balloon disposed on the opposite side of the catheter tip from the aperture. As the tip is placed in close proximity to the fatty material, the balloon is inflated to force the aperture into contact with the fatty material. When the blade is rotated, portions of the fatty material are shaved off and retained within the interior lumen of the catheter. This process is repeated until a sufficient amount of fatty material is removed and substantially normal blood flow is resumed.

In another procedure, stenosis within arteries and other body lumens is treated by permanently or temporarily introducing a stent into the stenosed region to open the lumen of the vessel. The stent typically has a substantially cylindrical tube or mesh sleeve made from such materials as stainless steel or nitinol. The design of the material permits the diameter of the stent to be radially expanded, while still providing sufficient rigidity such that the stent maintains its shape once it has been enlarged to a desired size.

Unfortunately, such percutaneous interventional procedures, i.e., angioplasty, atherectomy, and stenting, often dislodge material from the vessel walls. This dislodged material can enter the bloodstream, and may be large enough to occlude smaller downstream vessels, potentially blocking blood flow to tissue. The resulting ischemia poses a serious threat to the health or life of a patient if the blockage occurs in critical tissue, such as the heart, lungs, kidneys, or brain, resulting in a stroke or infarction.

In general, existing devices and technology have a number of disadvantages including high profile, difficulty using multiple parts and components that result in an involved procedure, manufacturing complexity, and complex operation of the device or system.

SUMMARY OF THE EXEMPLARY EMBODIMENTS OF THE INVENTION

Exemplary embodiments of the present invention illustrate vascular embolic protection devices that are configured for percutaneous insertion into a body lumen of a patient. The exemplary embodiments can be used with any surgical procedure requiring the use of a percutaneous device. Such procedures can include, by way of example and not limitation, angioplasty, atherectomy, and/or the introduction of a stent into a body lumen of a patient.

One or more of the configurations of the embolic protection device can meet criteria for both guide wires and embolic protection devices. For instance, it is desirable that a guide wire is steerable. Consequently, embodiments of the embolic protection device can be inserted into any body lumen of a patient and manipulated and steered by a physician to traverse the tortuous anatomy of the patient to a lesion or occlusion. Such body lumens can include, but are not limited to, a coronary artery, carotid arteries, renal arteries, bypass grafts, the superficial femoral artery, the arteries of the upper and lower extremities, cerebral vasculature, etc.

To assist the physician with the above-recited endeavor, one or more configurations of the embolic protection device can include a shapeable, soft, distal tip. In addition, the embolic protection device is capable of translating rotational movement or force applied to the proximal end thereof substantially equally to the distal end. In other words, with the embolic protection device positioned within a vessel of the patient, as a physician rotates the proximal end of the embolic protection device, the distal end of the embolic protection device rotates substantially simultaneously with the movement of the proximal end. This is typically defined as having a one-to-one torqueability.

Further, some embodiments of the exemplary embolic protection device can be kink resistant and capable of receiving a variety of different coatings to improve lubricity, have antithrombogenic properties, and/or reduce platelet aggregation. These coatings can include, but are not limited to, a hydrophilic coating, a heparinized coating, PTFE, silicone, or other coating known to those skilled in the art in light of the teaching contained herein.

In one exemplary embodiment, the embolic protection device can include a guide member having a distal end, a proximal end, and a lumen extending from the distal end to the proximal end. Additionally, the embolic protection device can include a filter assembly coupled to the guide member and having a proximal end and a distal end. The mechanism can have a plurality of struts, at least one of the struts being biased to extend outwardly. Each strut can be made from, by way of example and not limitation, stainless steel, metals, alloys, composites, plastics, polymers, synthetic materials, shape memory materials, combinations thereof, or other materials that allow the struts to perform one or more of the functions described herein.

The filter assembly can further include a filter media adapted to filter material from a blood stream coupled to at least two of the plurality of struts. The filter media can have an open proximal end and a closed distal end. A distal end of at least one strut can move independently of the other struts even with the filter material surrounding the struts.

The filter media of the device can be configured to capture material of a variety of sizes and enable removal of the captured material. To achieve this, filter media pore sizes and shapes can be selected based upon the size of material to be captured. The material to be captured can include but is not limited to, particulates, thrombi, any atherosclerosis or plaque material dislodged during a procedure, or other foreign material that may be introduced into the vasculature of the patient. The filter media can also be made from, by way of example and not limitation, a woven or braided plastic or metallic mesh, a perforated polymer film, a shape memory material, combinations thereof, or other material that is capable of capturing material within flowing blood, while allowing the blood to flow through the pores or apertures thereof.

The embolic protection device can also include a sleeve, at least partially surrounding the plurality of struts and the filter media, for restraining the filter device in a collapsed position during an insertion procedure. The embolic protection device can also include additional loops surrounding the struts to aid in restraining the filter device. In exemplary embodiments, the embolic protection device can also include a tether member or wire that secures both the sleeve and the additional loops.

The embolic protection device can be inserted into the body lumen of a patient in a collapsed position. Since at least one of the struts is biased to extend outward when the filter assembly is in an open position, the filter can then be deployed by at least partially removing the tether wire, thus releasing both the sleeve and the loops. In some embodiments, the tether wire can be completely removed.

An additional aspect of the embolic protection device is that the device can include one or more radiopaque markers attached to the struts, the filter media, and/or the guide member. These radiopaque markers enable the embolic protection device to more easily be seen on an X-ray or other device for viewing the interior of an object.

These and other objects and features of the present invention will become more fully apparent from the following description and appended claims, or may be learned by the practice of the invention as set forth hereinafter.

BRIEF DESCRIPTION OF THE DRAWINGS

To clarify further the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 8 illustrates an exemplary configuration of an embolic protection device cooperating with a capture catheter;

FIG. 9 illustrates an exemplary configuration of an embolic protection device at least partially cooperating with the capture catheter;

FIG. 10 illustrates an exemplary configuration of an embolic protection device further cooperating with the capture catheter;

FIG. 11 illustrates an exemplary configuration of an embolic protection device being captured by the capture catheter;

DETAILED DESCRIPTION OF THE EXEMPLARY EMBODIMENTS

The present invention generally relates to percutaneous embolic protection devices, systems, and methods of using the same. Embodiments of the present invention can be utilized in association with devices, systems, and methods for inserting an embolic protection device, such as but not limited to, a vascular embolic protection device, within any body lumen of a patient. The device can be easily inserted into a body lumen and deployed to capture potential embolic material. The device can then be captured and removed without reintroducing any of the captured embolic material back into the body lumen.

Figure 1:
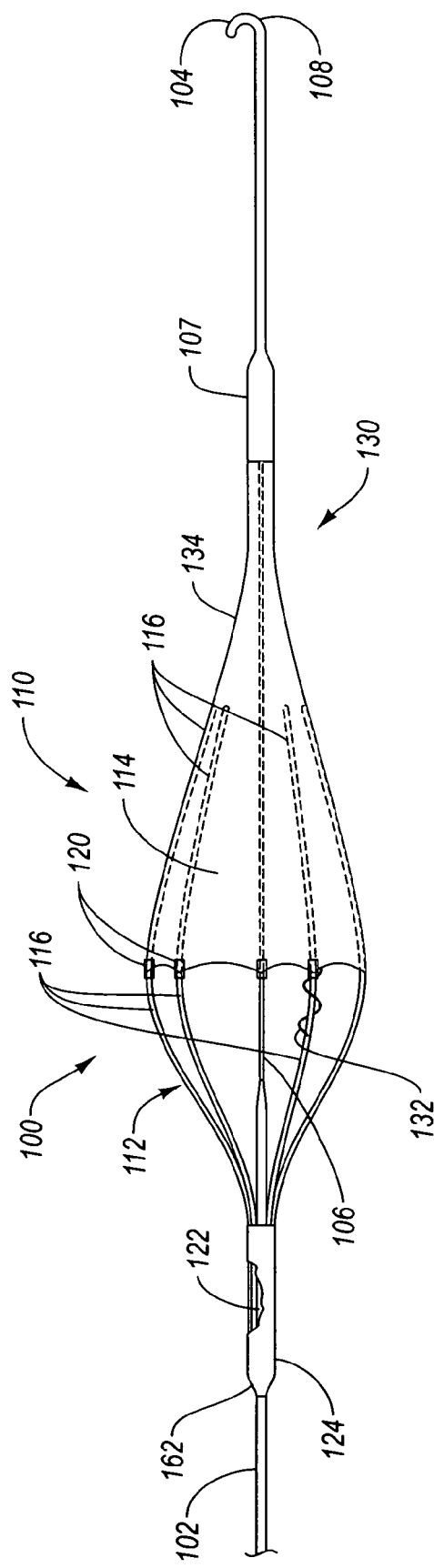
FIG. 1 illustrates an exemplary configuration of an embolic protection device.

FIG. 1 is a side view of a distal end of an exemplary embolic protection device 100. Embolic protection device 100 is capable of being inserted into any body lumen of a patient and function as a guidewire or exchange wire for other medical components or devices, such as, but not limited to, catheters, stents, balloons, atherectomy devices, or other components or devices that can be exchanged using a guidewire. Further, embolic protection device 100 can be used to filter particulates, as will be described in more detail hereinafter, thereby acting as an embolic protection device to provide embolic protection during a procedure.

The embolic protection device 100 includes an emboli capturing mechanism, such as a filter assembly 110, connected to the distal end of a guide wire, guide tube, or guide member 102. Illustratively, the term "guide member" can refer to a member that can be completely solid, such as a guidewire, a member that partially includes a lumen therein, or a member that includes a lumen extending from a proximal end to a distal end thereof, such as a hypo-tube. Consequently, the term "guide member" can include or encompass a guidewire or a hypo-tube that is configured to perform the functions described herein.

Guide member 102 can be fabricated from a variety of materials. For example, guide member 102 can be fabricated from shape memory materials. Shape memory materials are well known in the art for their ability to enable devices to assume one or more shapes depending on specific physical parameters to which the shape memory material may be exposed. A device constructed of one or more shape memory materials can be configured to transition from an initial shape to a secondary shape when the shape memory material is exposed to a known triggering condition. Examples of triggering conditions include specific predetermined temperatures, a specified pH, and other environmental conditions.

Shape memory materials suitable for use in fabrication of guide member 102, as well as other parts which will be discussed below, include, but are not limited to, shape memory polymers, shape memory metals, such as nitinol, and other materials both natural and synthetic. Several shape memory polymer materials may be suitable for fabrication of guide member 102. These materials include but are not limited to: polyurethane; polycycloocetene; cross-linked polyethylene; thermoplastics such as shape memory polyurethanes, polyethylene, polynorborene polymers and copolymers and blends thereof with styrene elastomer copolymers, such as Kraton, and cross-linked transpolyoctylene rubber; cross-linked polyisoprene; styrene butadiene copolymers; bioabsorbable shape memory polymers such as polycaprolactone, copolymers, and/or PLLA PGA copolymers; PMMA; Azo-dyes, Zwitterionic and other photo chromatic materials.

Alternatively, guide member 102 can be fabricated from steel, metals, metal alloys, composites, plastics, polymers, synthetic materials, or combinations thereof. Optionally, guide member 102 can be covered with a variety of different coatings, such as, but not limited to, coatings to improve lubricity or having anti-thrombogenic properties, reduce platelet aggregation, hydrophilic coatings, a heparinized coating, PTFE, silicone, or combinations thereof.

Illustratively, guide member 102 can have an outside diameter of between about 0.010 inches to about 0.035 inches, between about 0.014 inches to about 0.018 inches, or between about 0.010 inches to about 0.018 inches. In one configuration, the outside diameter of guide member 102 is about 0.014 inches. Similarly, when guide member 102 includes a lumen, the diameter of a lumen of guide member 102 can range from about 0.004 inches to about 0.029 inches or between about 0.008 inches to about 0.014 inches. In one configuration, the diameter of the lumen is about 0.008 inches.

Filter assembly 110 includes a filter basket 112 connected to a filter media 114. The filter basket 112 includes a body 122 with a plurality of resilient struts 116 extending from body 122 toward a distal end of embolic protection device 100. The distal ends of the struts 116 can remain detached one from another and so can move independently of one another, while such movement is at least partially constrained by filter media 114 attached to struts 116.

The struts 116 can be integrally formed with body 122. For instance, filter basket 112, including struts 116 and body 122, can be formed from a shape memory material tube, where a distal end of the tube can be cut to form struts 116. In another configuration, struts 116 attach to a separate body 122, such as a tube, forming part of filter basket 112, i.e., a proximal end of filter basket 112. In this latter case, struts 116 are attached to the separate body 122 using one or more of a variety of conventional attaching techniques, such as, but not limited to, an interference fit, adhesive, welding, soldering, solvent bonding, radio frequency or ultrasonic bonding, or a combination of these.

In addition to the above, struts 116 can attach to filter media 114 through a variety of techniques. For instance, struts 116 extend towards a distal end of embolic protection device 100 within an interior of filter media 114. In another configuration, struts 116 extend towards a distal end of embolic protection device 100 so that filter media 114 can be disposed within the basket formed by struts 116, i.e., an exterior of filter media 114 attaches to an interior surface of struts 116. In still another configuration, struts 116 can pass through filter media 114 one or more times between a proximal end and a distal end of filter media 114. Therefore, filter media 114 attaches to an exterior surface, an interior surface, or a combination of both the interior and exterior surfaces of each strut 116, such as when struts 116 are interwoven with filter media 114. In one exemplary embodiment, filter media 114 can attach to only the interior surfaces of struts 116. The struts 116 prevent damage to filter media 114 during capture, because a capture catheter moves along struts 116 rather than sliding over filter media 114. This prevents damage to filter media 114 that can result in filter media rupture and escape of captured emboli.

Suitable materials for constructing the struts 116 of filter basket 112, body 122, and/or filter basket 112 itself, include, but are not limited to, stainless steel, metals, alloys, composites, plastics, polymers, synthetic materials, shape memory materials, combinations thereof, or other materials that allow struts 116 to perform one or more of the functions described herein. The individual struts 116 can be heat set to shape, biasing them in the open position shown in FIG. 1. In one embodiment, one of struts 116 may have an atraumatic tip formed at the end thereof.

Figure 2:
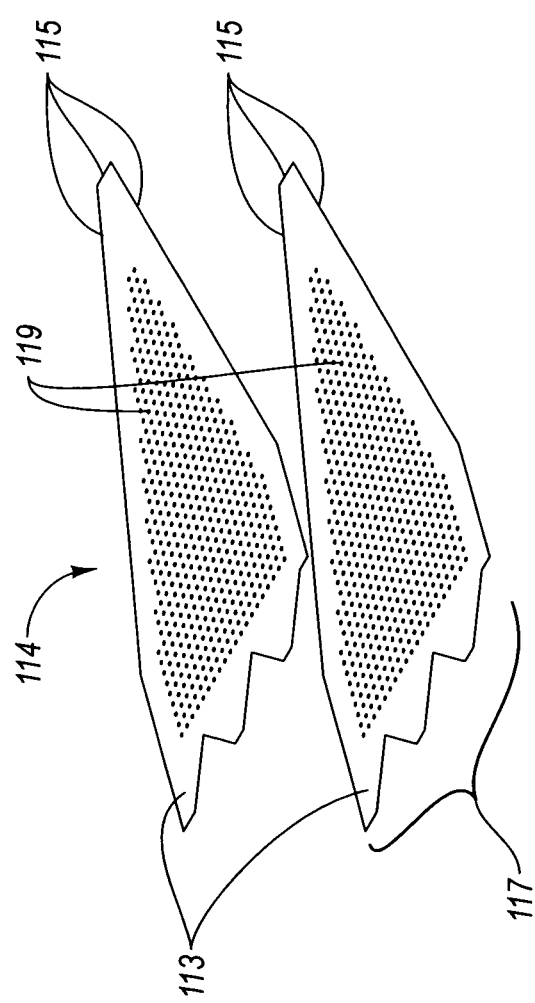
FIG. 2 illustrates a schematic representation of a filter media of the embolic protection device of FIG. 1.

With continued reference to FIGS. 1 and 2, a proximal, open end of filter media 114, having a generally conical or frustoconical form, attaches to one or more struts 116 of filter basket 112 by adhesive, thermal bonding or solvent bonding. A distal end of filter media 114 attaches to distal tip 104 at or about a point 107. Such attachment occurs with a mechanical fastener, such as a wire coil, adhesive, or a combination of both. This point 107 can also be built up with an amount of adhesive that provides a taper from the diameter of a coiled spring 108 of distal tip 104 to that of the constrained filter basket 112. The taper at point 107 may also be made from a pre-molded polymer material.

The distal end of guide member 102 can be inserted into filter basket 112 and held in place with an interference fit, adhesive, welding, soldering or a combination of these. Other methods of connecting the proximal end of struts 116 to guide member 102 include ultra violet curable adhesives, acrylics, cyanoacrylates, solvent bonding, radio frequency or ultrasonic bonding, and the like.

The distal tip 104 of embolic protection device 100 is made from a core member or wire 106, which can be ground to a shape that influences the flexibility of the tip, and coiled spring 108 that can be soldered or welded to core wire 106. For instance, guide member 102 can be disposed within a proximal portion or lumen of filter basket 112, while distal tip 104 can be inserted into a portion of or all of the remaining distal lumen of filter basket 112 and can be held in place by an interference fit, adhesive, welding, soldering or a combination of these.

In one embodiment, filter assembly 110 has parts inherent or added to aid in its radiopacity. This coil 108 of distal tip 104 can be made from a radiopaque material. Bands 120 of a radiopaque material can be added to at least one of struts 116 of filter basket 112. The bands, 120, may be made from cut tubing of a radiopaque material, or optionally be made from a section of helically wound coil of a radiopaque material. Optionally, a band 124 of radiopaque material, similar to band 120, can also be added at the proximal junction of filter basket 112 and guide member 102. This band 124 can optionally surround at least a portion of body 122 and can be encapsulated in an adhesive filet to provide a smooth transition in outer diameters. The radiopaque substances can include, but not limited to, barium sulphate, bismuth subcarbonate, titanium dioxide, combinations thereof, or other radiopaque substances.

Figure 3:
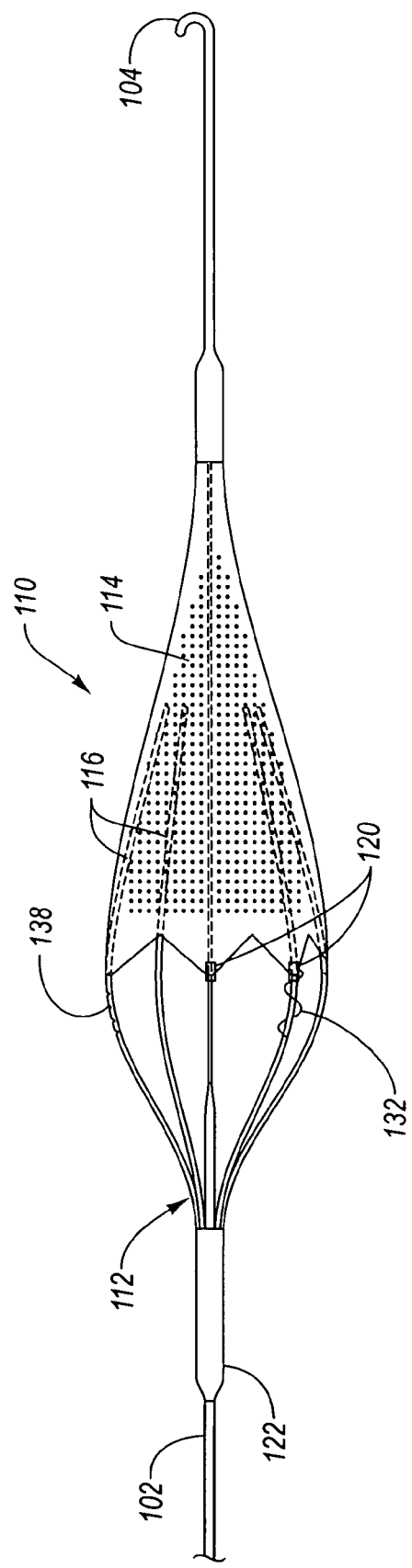
FIG. 3 is a more detailed representation of the exemplary configuration of the embolic protection device of FIG. 1.

FIGS. 2 and 3 show the construction of exemplary filter media 114 from multiple pieces of generally flat cut polymer film 113. A pattern of holes, pores, or apertures 119 can be cut in each flat piece of filter media 114 to allow for filtration during use. The outer edges 115 of two pieces of film 113 can be bonded together making a two-layer membrane that can be opened at the un-bonded edge 117 to create filter media 114, shown in FIGS. 1 and 3. Various methods and manners are known to bond two pieces of polymer film. For instance, adhesive, ultra violet curable adhesives, acrylics, cyanoacrylates, solvent bonding, radio frequency or ultrasonic bonding, or a combination of these.

Although reference is made to use of a polymer film as filter media 114, one skilled in the art will understand that various materials can be used to form filter media 114. For instance, filter media 114 can be fabricated from a variety of different materials, such as, but not limited to, a woven or braided plastic or metallic mesh, a perforated polymer film, a shape memory material or mesh, combinations thereof, or other material that can be capable of capturing material within flowing blood, while allowing the blood to flow through the pores or apertures thereof. Consequently, the manner by which edges are bonded together may also vary based upon the materials used to form filter media 114. Generally, filter media 114 can be fabricated from a variety of materials so long as the filter media is capable of being packed within filter basket 112, and optionally floating in the blood flow or stream passing through the body lumen within which it can be inserted, and being biocompatible.

Filter media 114 can have a variety of differently sized holes or pores 119 ranging from about 50 microns to about 200 microns, from about 60 microns to about 180 microns, or from about 75 microns to about 150 microns. The pores can have a variety of different configurations. For instance, the pores can be circular, oval, polygonal, combinations thereof, or other configurations known to one skilled in the art in light of the teaching contained herein. In one configuration, filter media 114 can include pores that are differently sized and configured. Consequently, a major or minor axis of each pore can have a variety of different sizes ranging from about 50 microns to about 200 microns, from about 60 microns to about 180 microns, or from about 75 microns to about 150 microns. Generally, the pore size can vary as needed, so long as the pores are sized (i) so that the pores do not compromise blood flow through the filter, i.e., prevent or severely restrict blood flowing through the filter, and (ii) collect material that could potentially occlude smaller downstream vessels, potentially blocking blood flow to tissue or result in stroke or infarction. In addition to the above, filter media 114 can be coated with a hydrophilic coating, a heparinized coating, PTFE, silicone, combinations thereof, or various other coatings as know or desired by one skilled in the art in light of the teaching contained herein.

Also shown in FIG. 3 are features 138 that are cut into the profile of struts 116 to provide location points for a plurality of loops 132 and/or radiopaque marking bands 120. These features 138 can include notches, grooves, or other structures that aid with placing loops 132 and radiopaque marking bands 120.

Figure 4:
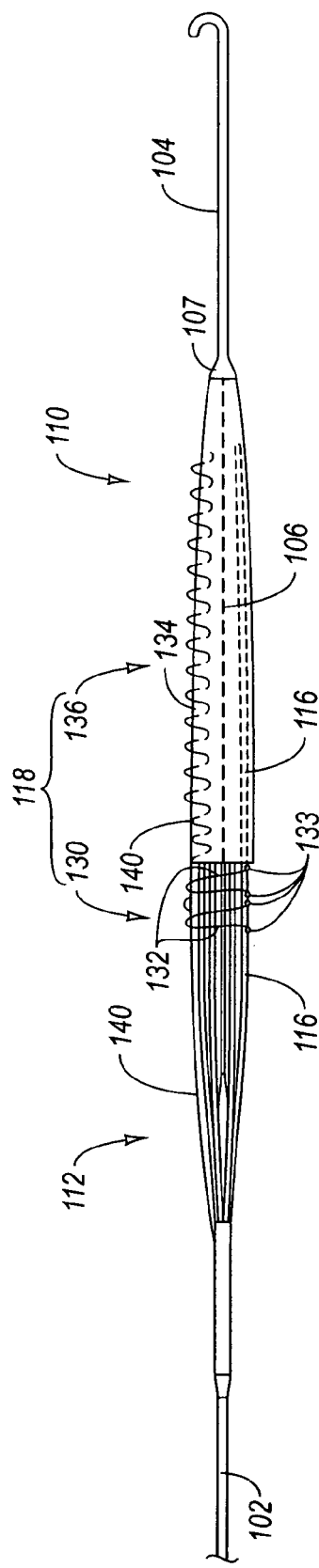
FIG. 4 illustrates a schematic representation of a side view of a distal end of the embolic protection device of FIG. 1 in a closed configuration.

With reference now to FIG. 4, before filter assembly 110 is deployed, struts 116 are maintained in a constrained or undeployed position by a restraining mechanism or constraining mechanism 118. Only one strut 116, shown in dotted lines, is depicted as being within restraining or constraining mechanism 118 for clarity and ease of explanation. The restraining mechanism or constraining mechanism 118 can use a combination of a first constraining mechanism 130 and a second constraining mechanism 136 to limit movement of struts 116. Generally, first constraining mechanism 130 and second constraining mechanism 136 can collectively or individually be referred to and/or function as restraining mechanism or constraining mechanism 118.

The first constraining mechanism 130 includes a plurality of loops of material 132 or loops 132 attached to or surrounding one or more of the struts 116. In one exemplary embodiment, loops 132 are attached to a single strut 116 at multiple attachment points 133. In between each attachment point 133 are loops 132. In some exemplary embodiments, loops 132 can be suture material. Alternately, loops 132 can be wire, an elastomeric material and any other material capable of securing struts 116 in a closed position. When in a closed position, loops 132 are held together by a tether member or wire 140. Tether wire 140 can also be a suture material, a thin metal wire, or other wire-like material.

This tether wire 140 can also cooperate and form part of second constraining mechanism 136 that constrains struts 116 and filter media 114 (FIG. 1). The second constraining mechanism 133 can include a sleeve of polymer material 134 and the tether wire 140 and functions to restraining movement of struts 116 until tether wire 146 is disengaged from sleeve 134. For simplicity in discussion, sleeve 134 is not shown in FIGS. 1-3, but it will be understood that sleeve 134 can remain attached to filter assembly 110 following removal of tether wire 140.

As shown in FIG. 4, a proximal end of sleeve 134 can attach to one or more struts 116. Optionally, sleeve 134 can attach to a proximal end of filter basket 112 and/or a distal end of guide member 102. The distal end of sleeve 134 is incorporated into the distal bond of filter media 114 (FIG. 1) to core wire 106, illustrated by dotted lines, at point 107. The intermediate portions of filer media 114 (FIG. 1) are a selectively maintained together so as to apply a restraining force of strut 116 wherein tether wire 140 can be stitched or interwoven through sleeve 134.

The actuating mechanism (not shown) cooperates with restraining device 118 to selectively release restraining device 118 when filter assembly 110 is deployed, as will be discussed in more detail hereinafter. Restraining device 118 provides two examples of means for restraining the deployment of filter assembly 110 until an operator desires to deploy the filter. Sleeve 134 is held in place with tether wire 140 can be one example of such means. Loops 132 provide an additional means of restraining filter assembly 110.

FIG. 4 clearly shows the loops 132 of constraining mechanism 130. The material forming loops 132 surrounds one or more of struts 116, such that when loops 132 are generally aligned, the material forming loops 132 applies a constraining force against struts 116. This constraining force is maintained by tether wire 140. The wire 140 passes through loops 132 when in the constrained position. Compressing struts 116 radially inwardly is the combination of loops 132, sleeve 134 pulled around filter media 114 (FIG. 1), and tether wire 140 threaded through loops 132 and stitched through sleeve 134.

The tether wire 140 terminates, in this exemplary configuration, within the quantity of adhesive at point 107, which provides a taper from the diameter of the coiled spring 108 of distal tip 104 to that of the constrained filter basket 112. Alternatively, tether wire 140 can terminate proximal to a distal end of embolic protection device 100, outside of the adhesive. In either case, when a proximal force is applied to tether wire 140, the end of wire 140 disengages from and is pulled through the stitched holes in sleeve 134 and loops 132.

To release struts 116 of filter basket 112, thereby allowing struts 116 to expand outwardly and deploy filter media 114, tether wire 140 can be moved proximally to remove tether wire 140 from engaging with loops 132. By removing the restraining force supplied by tether wire 140, sleeve 134 opens and loops 132 no longer prevent struts 116 from expanding outwardly. Consequently, moving tether wire 140 in a proximal direction, and optionally completely removing tether wire 140 from embolic protection device 100, releases the forces applied by sleeve 134 and loops 132 in preventing struts 116 from moving outwardly.

Figure 5:
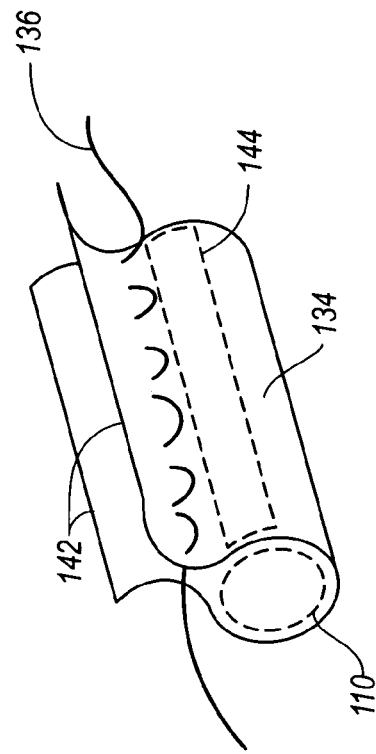
FIG. 5 illustrates a schematic perspective view of a portion of a constraining mechanisms of the embolic protection device of FIG. 1.

Illustratively, FIG. 5 depicts one exemplary method of constructing sleeve 134 that constrains the distal portion of filter basket 112, struts 116, and filter media 114. The struts 116 and filter media 114 are shown as a compressed and bundled assembly 110 with sleeve 134 surrounding assembly 110. In this configuration, sleeve 134 can be made from a film of polymer. The sleeve 134 is stitched closed with tether wire 140, as shown. The flaps 142 of sleeve 134 that remain after stitching can be either cut or folded down onto an area 144, (only one side shown) and secured in place with adhesive or wrapped entirely around sleeve 134 and bonding the flaps 142 to each other using adhesive or thermal bonding.

Other embodiments are contemplated for constructing a restraining mechanism or constraining mechanism 118 for restraining or constraining struts 116 of filter basket 112 before filter media 114 is deployed. Such mechanisms are described in U.S. patent application Ser. No. 10/186,275, filed Jun. 28, 2002, and entitled "Methods, System, And Devices for Providing Embolic Protection and Removing Embolic Material," and U.S. patent application Ser. No. 10/290,099, filed Nov. 7, 2002, and entitled "Methods, Systems, and Devices for Delivering Stents," which applications are incorporated herein by reference.

Figure 6:
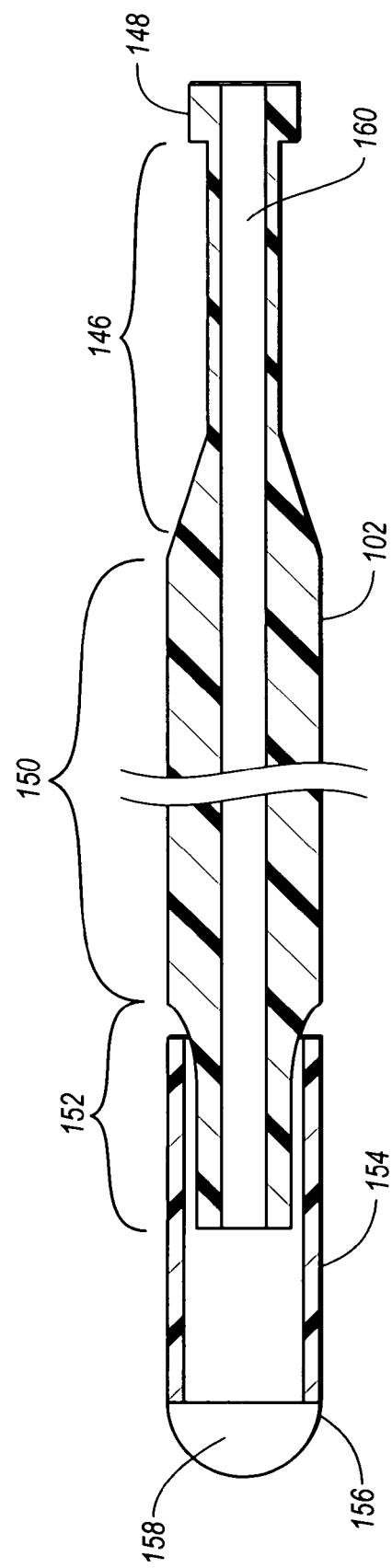
FIG. 6 illustrates a schematic representation of a cross-sectional side view of a distal end of the guide member of the embolic protection device of FIG. 1.

FIG. 6 illustrates a representative sectional view of the length of the guide member 102. The distal segment 146 has an outer diameter modified to reduce the stiffness of this segment and has a different diameter distal tip 148, which can be sized to create a tight bond with body 122 of filter basket 112, which was shown and discussed in FIG. 1. This distal segment 146 has an outer surface coated with a lubricous material to reduce friction during use. The main body 150 of guide member 102 can also be coated with a lubricious material to reduce friction during use. The proximal segment 152 of guide member 102 has an outer diameter reduced as well to allow an actuation handle 154 to fit over proximal segment 152, while not increasing the net outer diameter of embolic protection device 100 to be larger than that of main body 150 of guide member 102. The tether wire (not shown) extends through an inner lumen 160 of guide member 102 to a proximal end 156 of actuation handle 154 where it connects to handle 154 either in a welded, crimped, or soldered joint 158, which provides a closed proximal end.

Although handle 154 is depicted as being a "female" type component, i.e., that receives another component, and proximal segment 152 is depicted as a "male" type component, i.e., that is inserted into another component, one skilled in the art will understand that handle 154 can be a "male" type component and proximal segment 152 can be a "female" type component. Further, handle 154 and proximal segment 152 can each have structures that function as a "male" type component or a "female" type component.

Figure 7:
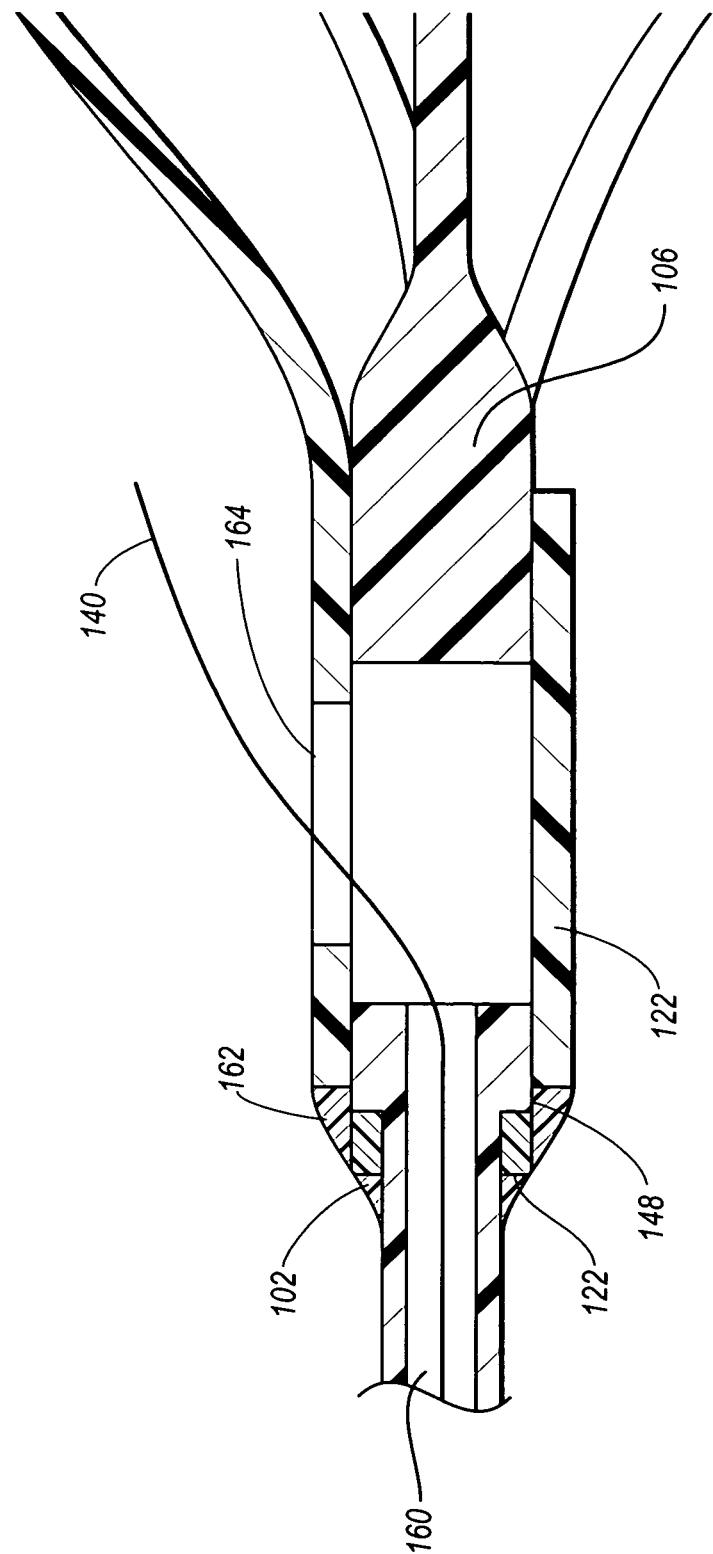
FIG. 7 illustrates a schematic representation of a cross-sectional side view of a distal end of the guide member of the embolic protection device of FIG. 1.

FIG. 7 shows a detailed cross section of the joints between guide member 102, filter basket 112, and core wire 106 of distal tip 104. An aperture 164 is cut into a sidewall of the proximal end of filter basket 112, i.e., the tubular body 122 of filter basket 112. This aperture 164 forms part of a path for tether wire 140 to extend from its attachment point at actuation handle 156 (FIG. 6), through lumen 160 of guide member 102, and back out to the side wall of filter basket 112, where it cooperates with loops 132 (FIG. 4) and/or sleeve 134. In addition, a sloped transition portion 162 is placed at a proximal end of filter basket 112 to ease the transition between the diameters of filter basket 112 and guide member 102. The transition portion of 162 can be an adhesive, such as an ultraviolet curable acrylic, an epoxy, a pre-molded polymer, or other structure or material to provide the desired transition. In another embodiment, tether wire 140 may be disposed on the outer surface of guide member 102 from a proximal end thereof towards a distal end thereof. Further, core wire 106 can include an aperture through which passes tether wire 140, before tether wire 140 cooperates with loops 132 and/or sleeve 134.

Exemplary embodiments of the present invention also relate to a capture mechanism for capturing filter assembly 110 after it has been deployed and after the embolic debris has been captured in filter media 114. One exemplary capture mechanism can be a capture catheter 200, illustrated with respect to FIGS. 8 through 16.

FIG. 8 depicts a distal tip of capture catheter 200 in cooperation with filter assembly 110. The distal end of capture catheter 200 has a tip 201 through which a lumen extends. This lumen facilitates the insertion of guide member 102 of embolic protection device 100 therein. This tip 201 is configured to function as a stop for capture catheter 200. By having a lumen whose diameter is smaller than a proximal end of filter assembly 110, capture catheter 200 is prevented or stopped from passing filter assembly 110 and causing particulates to be forced out of filter assembly 110. Although tip 201 is illustrated as being tapered, one skilled in the art will appreciate that non-tapered configurations are also possible.

A capture sleeve 202 surrounds tapered tip 201 of capture catheter 200. The distal end of this capture sleeve 202 contains a radiopaque marker, such as, but not limited to, a cut tubing band 204. The capture sleeve 202 can slide over and extend past tapered tip 201. This enables sleeve 202 to extend around filter assembly 110 and cause struts 116 to collapse, thereby trapping the particulates and emboli within filter assembly 110.

FIGS. 8 through 11 show a sequence of filter assembly 110 being captured by capture sleeve 202 that telescopes over tapered tip 201. FIG. 9 shows capture sleeve 202 extended distally over tapered tip 201 almost to engage struts 116 of filter assembly 110. Before capture sleeve 202 is moved distally, a proximal portion of capture catheter 200 and a proximal portion of device 100 are held in reference one to another thereby preventing inadvertent movement of capture catheter 200 relative to device 100 during deployment of capture sleeve 202. The proximal portion of capture catheter 200 and the proximal portion of device 100 can be held "wire-on-wire" by way of a clamp, a hemostasis valve associated with capture catheter 200 or otherwise used during the procedure, by the physician, by a hemostat selectively mounted to or forming part of capture catheter 200 and/or device 100, or some other clamping means for maintaining the relative position of one structure to another structure, i.e., the relative position of the proximal end of capture catheter 200 and the proximal end of device 100.

In FIG. 10, capture sleeve 202 has extended further to collapse struts 116 and enclose proximal opening of filter media 114. As capture sleeve 202 engages with struts 116, and prior to engaging filter media 114, capture sleeve 202 causes a proximal end of filter media 114 to collapse to prevent migration of collected emboli into the body lumen. Stated another way, before emboli can escape from within an interior of filter media 114 under the forces exerted by capture sleeve 202, capture sleeve 202 closes the proximal end of filter media 114 by causing struts 116 to move toward each other. This can be aided through curvature of struts 116 and position of filter media 114 or struts 116. For instance, the more acute the angular orientation of a proximal end of struts 116 relative to a longitudinal axis of guide member 102, the more quickly the proximal end of filter assembly 110 closes. Further, the more acute the angular orientation of a proximal end of struts 116 relative to a longitudinal axis of guide member 102, the lesser the longitudinal displacement of capture catheter 200 needed to close the proximal end of filter assembly 110. Various angular orientations are possible based upon the particular configuration of device 100 and the speed desired to close filter assembly 110.

To completely capture filter media 114, and the collected emboli, capture sleeve 202 can be moved in the distal direction. The capture catheter 202 can be moved distally until filter media 114 of filter assembly 110 is completely encapsulated by capture sleeve 202, as illustrated in FIG. 11.

Figure 12:
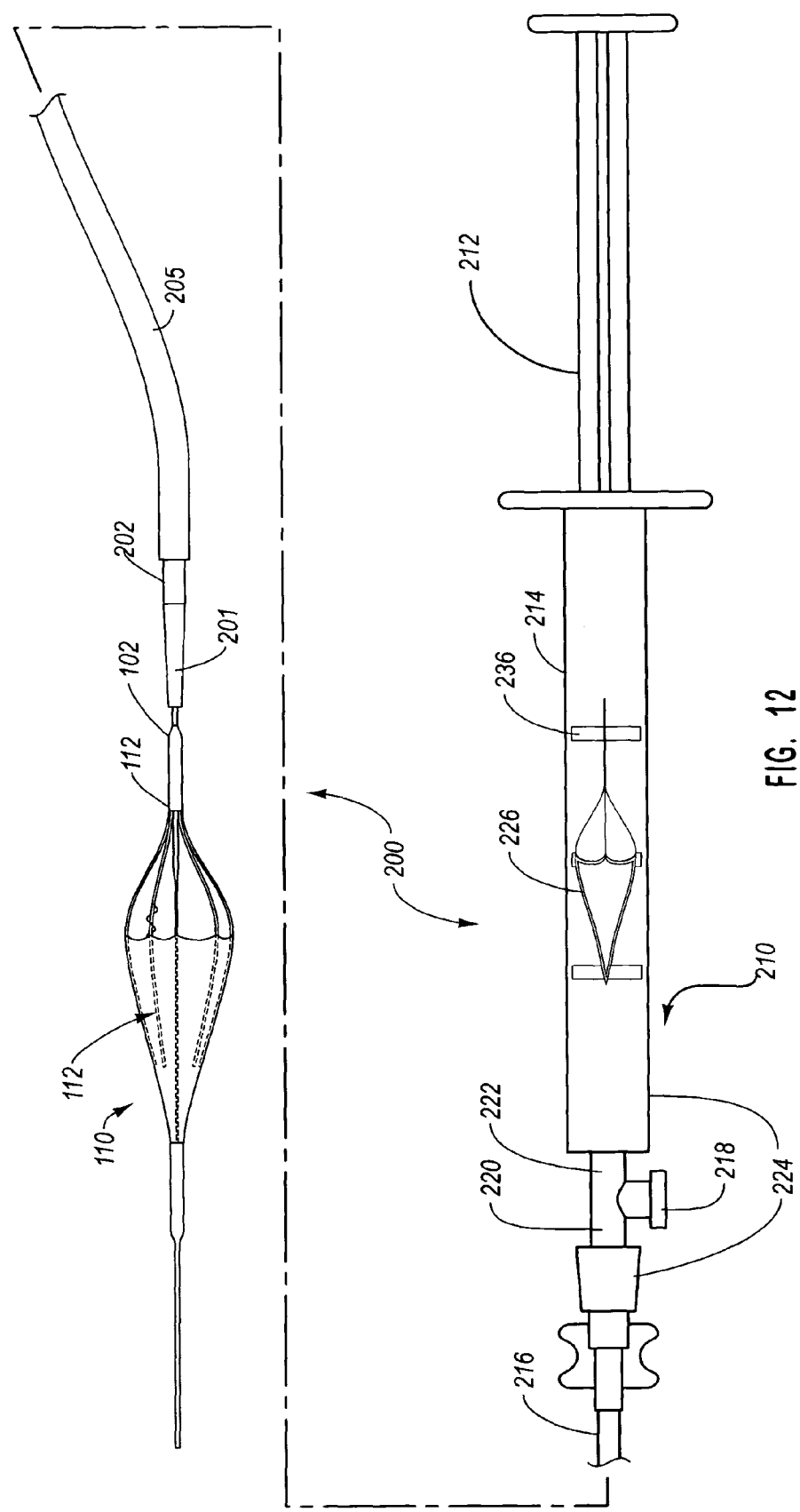
FIG. 12 illustrates a proximal end and a distal end of the capture catheter of the present invention as it cooperates with the embolic protection device of FIG. 1.

FIG. 12 shows a mechanical actuator 210 at a proximal end of capture catheter 200. The mechanical actuator 210 includes a plunger 212 disposed within a barrel 214. The plunger 212 connects by a control wire (not shown) through a lumen (not shown) of the hollow, metallic, catheter shaft 216 to capture sleeve 202 at the distal end of capture catheter 200, which is inserted in a guide catheter 205 as capture catheter 200 would be used clinically. The barrel 214 of actuator 210 is connected by luer fittings 224 to catheter shaft 216. A figure or image 226 depicting the shape of filter assembly 110 is printed or attached to barrel 214 of actuator 210. In conjunction with a reference marker 236 that indicates the distal end of plunger 212, actuator 210 provides a visual reference that correlates the position of plunger 212 with respect to the position of capture sleeve 202 and the actual filter assembly 110. A luer fitting 218 is provided to allow catheter shaft 216 and capture sleeve 202 to be aspirated prior to use. This is accomplished through a hole (not shown) in catheter shaft 216 near position 220 internal to luer fitting 218. A valve or seal 222 disposed proximal to luer fitting 218 prevents fluid from going into actuator barrel 214 during the aspiration process.

Figure 13:
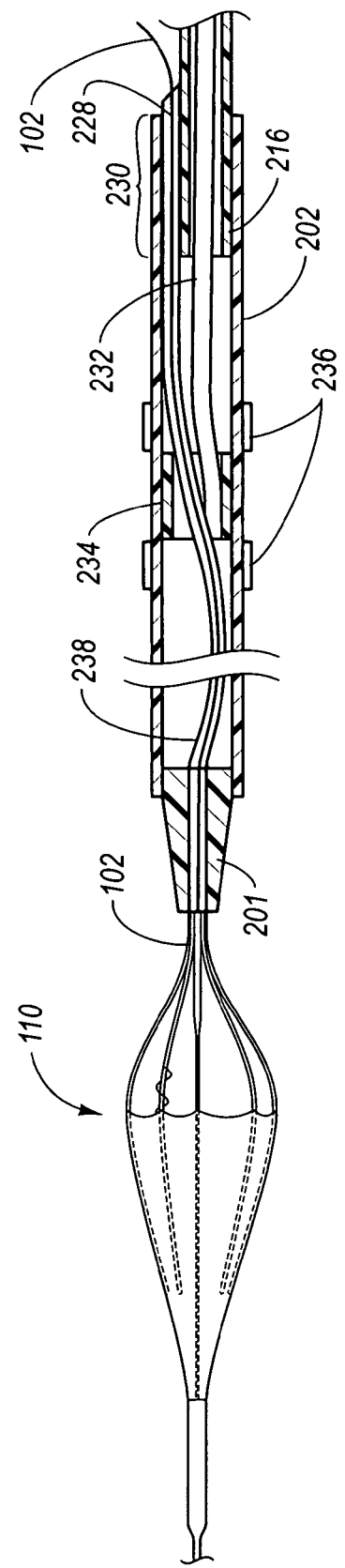
FIG. 13 illustrates a schematic cross-sectional side view of the capture catheter cooperating with the embolic protection device of FIG. 1.

FIG. 13 is a partial sectional view of the interfaces between the proximal and distal components of capture catheter 200. A tube 228, which connects catheter shaft 216 to tapered tip 201, is bonded to a distal end of catheter shaft 216 to facilitate rapid exchange of capture catheter 220 over guide member 102. Alternately, tube 228 can have a length similar to the length of capture catheter 200, where an over the wire exchange is to occur. This tube 228 provides a lumen through which extends guide member 102 of filter assembly 110. A control member or wire 232, which is attached at the proximal end to plunger 212 (FIG. 13), connects to a tubing section 234 through one of a variety of bonding or connecting techniques, such as, but not limited to, adhesives, welds, solders, fasteners, or combinations thereof. This tubing section 234 connects, in turn, to capture sleeve 202 through adhesives, welds, solders, fasteners, or combinations thereof. The tubing section 234 is further secured in place by external bands 236 on both the proximal and distal sides of capture sleeve 202. The telescoping action of capture catheter 200 is accomplished by pressing on plunger 212 that pushes capture sleeve 202 distally with respect to the parts that are connected to barrel 214, catheter shaft 216, tube 228, and tapered tip 201. For instance, moving plunger 212 causes control wire 232 to move distally. Since control wire 232 is attached to tubing section 234, which is connected to capture sleeve 202, movement of control wire 232 distally moves tubing section 234 and capture sleeve 202 distally. The reverse is also possible.

Figure 14:
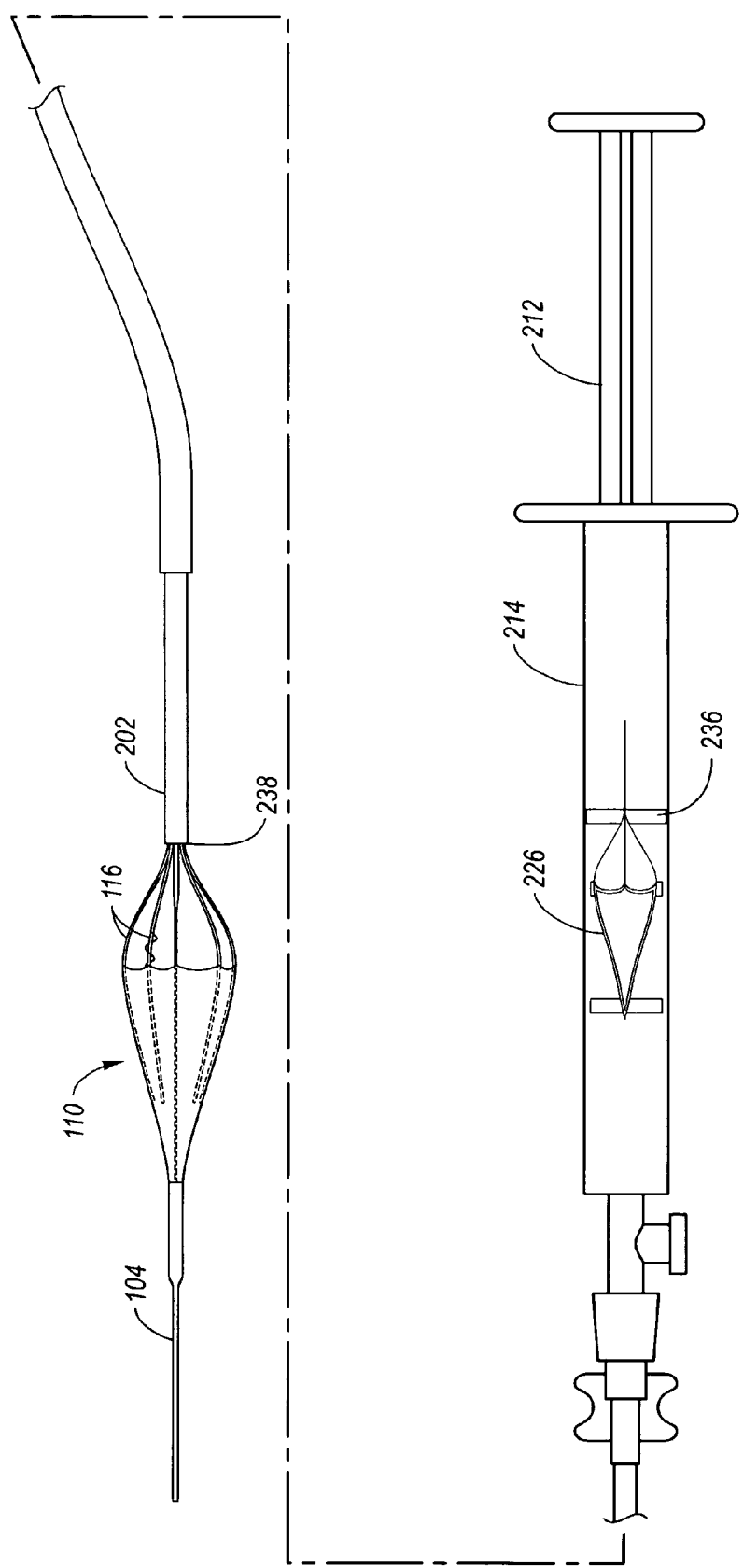
FIG. 14 illustrates the proximal end and the distal end of the capture catheter of the present invention as it cooperates with the embolic protection device of FIG. 1.

FIGS. 12 and 14-16 show the sequence of using capture catheter 200 with embolic protection device 100. In FIG. 12, filter basket 112 of filter assembly 110 is brought next to tapered tip 201 of capture catheter 200 by inserting guide member 102 of filter assembly 110 through the lumen in tapered tip 201. In FIG. 14, plunger 212 is depressed with respect to barrel 214 until capture sleeve 202 is just proximal to struts 116 of filter assembly 110. The reference mark 236 provides a correlation between the distal end 238 of capture sleeve 202 and embolic protection device 100 and the FIG. 226 on barrel 214 of capture actuator 210.

Figure 15:
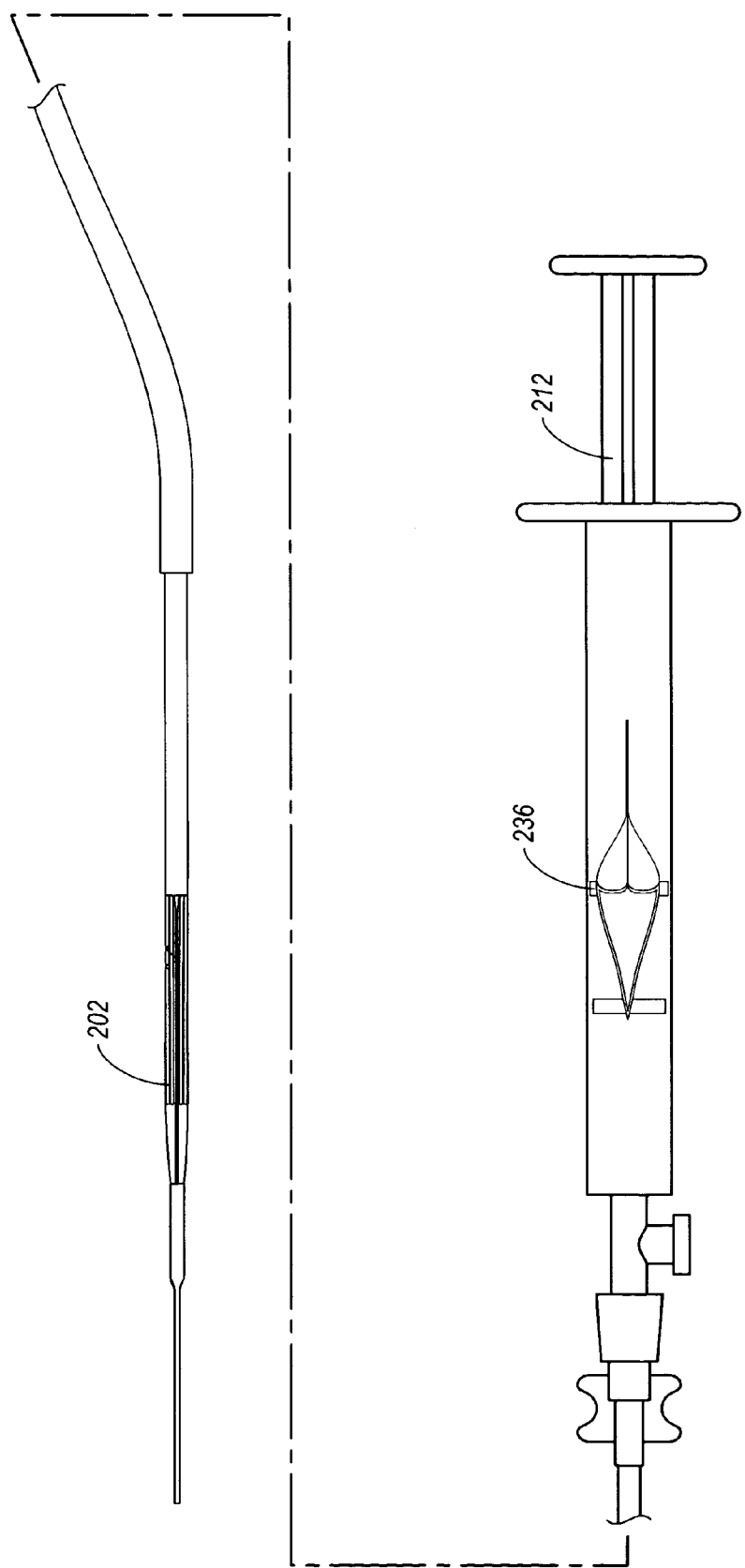
FIG. 15 illustrates the proximal end and the distal end of the capture catheter as it further cooperates with the embolic protection device of FIG. 1.
Figure 16:
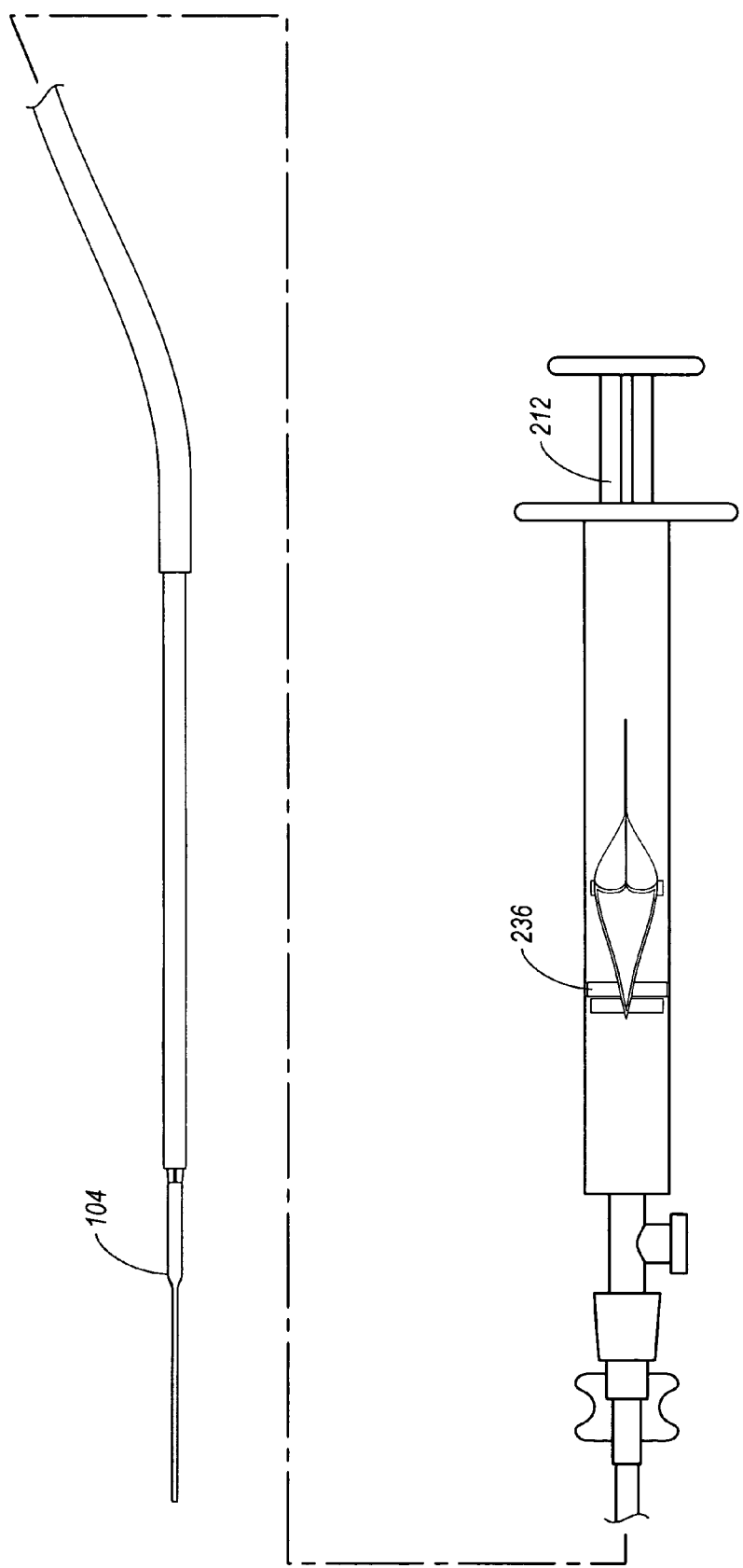
FIG. 16 illustrates the proximal end and the distal end of the capture catheter of the present invention as it substantially captures the embolic protection device of FIG. 1.

In FIG. 15, plunger 212 has been pressed until reference mark 236 aligns with a proximal end of FIG. 226 on barrel 214, illustrating a proximal end of filter media 114. This point corresponds with capture sleeve 202 enclosing the proximal opening of filter media 114. FIG. 16 shows plunger 212 completely depressed. Capture sleeve 202 has now completely encapsulated filter assembly 110 save distal tip 104, which is still visible.

Additional description relating to capture catheter 200 of the present invention can be found in U.S. patent application Ser. No. 10/832,565, filed on Apr. 27, 2004, and entitled "Slidable Capture Catheter", which disclosure is herein incorporated by reference in its entirety.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A filter device for percutaneous insertion into a blood vessel during a procedure, the filter device comprising:
    (a) a guide member comprising a distal end, a proximal end, and a lumen extending from the distal end to the proximal end;
    (b) filtering means for filtering material from a blood stream, said means being coupled to said guide member and having a proximal end and a distal end;
    (c) a first restraining means for restraining said filtering means, wherein said first restraining means comprises a sleeve at least partially surrounding said filtering means, wherein said sleeve is releasably secured with a tether wire, said tether wire passing through a plurality of openings in said sleeve, said tether wire being at least partially releasable by an operator to allow deployment of said filter; and (d) a second restraining means for restraining said filtering means, said second restraining means cooperating with said first restraining means in restraining said filtering means in an undeployed position.

2. The filter device of claim 1, wherein said filtering means comprises:
  (a) a plurality of struts extending from said distal end of said guide member, at least one of said plurality of struts being biased to extend outwardly, and a distal end of at least one strut of said plurality of struts moving independently of the other struts of said plurality of struts; and
  (b) a filter media coupled to at least two of said plurality of struts, said filter media comprising a plurality of pores configured to filter material from a blood stream.

3. The filter device of claim 2, wherein said filter media comprises at least one of a woven plastic mesh, a braided plastic mesh, a woven metallic mesh, a braided metallic mesh, a perforated polymer film, and a shape memory material mesh.

4. The filter device of claim 2, wherein said plurality of pores are at least one of circular, oval and polygonal in shape.

5. The filter device of claim 4, wherein said pores are sized and configured to allow blood to flow through said filter media while blocking an occlusive material.

6. The filter device of claim 5, wherein said pores are between 50 and 200 micrometers in diameter.

7. The filter device of claim 1, wherein said sleeve is secured at a distal end to at least one of said struts and a core member.

8. The filter device of claim 1, wherein said sleeve is secured at a proximal end to at least one of said struts.

9. The filter device of claim 1, wherein said second restraining means comprises at least two loops, said loops passing around a plurality of said struts to hold said filter in a undeployed position.

10. The filter device of claim 9, wherein said tether wire secures said loops around said plurality of struts.

11. The filter device of claim 1, wherein said guide member is steerable through the blood vessel.

12. The filter device of claim 11, wherein said guide member further includes a soft tip at said distal end.

13. A filter device for percutaneous insertion into a blood vessel during a procedure, the filter device comprising:
  (a) a guide member comprising a distal end, a proximal end, and a lumen extending from the distal end to the proximal end;
  (b) a filter assembly for filtering material from a blood stream, said filter assembly being fixedly attached to said guide member and having a proximal end and a distal end;
  (c) a first restraining device for selectively restraining said filter assembly, wherein said first restraining device comprises a sleeve at least partially surrounding said filter assembly, wherein said sleeve is releasably secured with a tether member, said tether member passing through a plurality of openings in said sleeve; and
  (d) a second restraining device for selectively restraining said filter assembly.

14. The filter device of claim 13, wherein said filter assembly further comprises:
  (a) a plurality of struts extending from said distal end of said guide member, at least one of said plurality of struts being biased to extend outwardly, and a distal end of at least one strut of said plurality of struts moving independently of the other struts of said plurality of struts; and
  (b) a filter media coupled to at least two of said plurality of struts, said filter media selectively filtering material from a blood stream and having an open proximal end and a closed distal end.

15. The filter device of claim 14, wherein said sleeve is secured at a proximal end to at least one of said struts.

16. The filter device of claim 14, wherein said second restraining device comprises at least two loops, said loops passing around a plurality of said struts to hold said filter in a desired position.

17. The filter device of claim 16, wherein said tether wire secures said loops around said plurality of struts.

18. The filter device of claim 13, wherein said sleeve is secured at a distal end to said distal end of said guide member.

19. A filter device for percutaneous insertion into a blood vessel during a procedure, the filter device comprising:
  (a) a guide member comprising a distal end, a proximal end, and a lumen extending from the distal end to the proximal end;
  (b) a filter assembly for filtering material from a blood stream, the filter assembly including a plurality of struts and a filter media, the filter assembly being fixedly attached to said guide member and having a proximal end and a distal end;
  (c) a sleeve for restraining the filter assembly, wherein the sleeve at least partially surrounds the filter assembly,
  (d) a tether wire releasably secured with the sleeve, the tether wire passing through a plurality of openings in the sleeve, the tether wire being at least partially releasable by an operator to allow deployment of the filter assembly.

20. The filter device of claim 19 further comprising at least two restraining loops for restraining said filter assembly, wherein the at least two restraining loops hold the filter assembly in a desired position.

21. The filter device of claim 19, wherein the plurality of struts extend from the distal end of said guide member, at least one of the plurality of struts being biased to extend outwardly, and a distal end of at least one strut of the plurality of struts moving independently of the other struts of the plurality of struts, and the filter media coupled to at least two of the plurality of struts, the filter media comprising a plurality of pores configured to filter material from a blood stream.

22. The filter device of claim 21, wherein said sleeve is secured at a distal end to at least one of said struts and a core member.

23. The filter device of claim 21, wherein said sleeve is secured at a proximal end to at least one of said struts.

24. The filter device of claim 19, wherein said filter media comprises at least one of a woven plastic mesh, a braided plastic mesh, a woven metallic mesh, a braided metallic mesh, a perforated polymer film, and a shape memory material mesh.

25. A filter device for percutaneous insertion into a blood vessel during a procedure, the filter device comprising:
  (a) a guide member comprising a distal end, a proximal end, and a lumen extending from the distal end to the proximal end;
  (b) a filter assembly for filtering material from a blood stream, the filter assembly including a plurality of struts and a filter media, the filter assembly being coupled to said guide member and having a proximal end and a distal end;

(c) a restraining sleeve for restraining the filter assembly, wherein the sleeve at least partially surrounding the plurality of struts and filter media; and (d) at least two restraining loops for restraining the filter assembly, the at least two restraining loops passing around a plurality of the struts to hold the filter assembly in an undeployed position.

26. The filter device of claim 25 further comprising a tether wire, wherein the sleeve is releasably secured with the tether wire, the tether wire passing through a plurality of openings in the sleeve, the tether wire being at least partially releasable by an operator to allow deployment of said filter assembly.

27. The filter device of claim 26, wherein the plurality of struts extend from the distal end of said guide member, at least one of the plurality of struts being biased to extend outwardly, and a distal end of at least one strut of the plurality of struts moving independently of the other struts of the plurality of struts, and the filter media coupled to at least two of the plurality of struts, the filter media comprising a plurality of pores configured to filter material from a blood stream.

28. The filter device of claim 27, wherein said sleeve is secured at a distal end to at least one of said struts and a core member.

29. The filter device of claim 27, wherein said sleeve is secured at a proximal end to at least one of said struts.

30. The filter device of claim 26, wherein said filter media comprises at least one of a woven plastic mesh, a braided plastic mesh, a woven metallic mesh, a braided metallic mesh, a perforated polymer film, and a shape memory material mesh.

* * * * *